United States Patent [19]

Gokcen

[11] 4,301,676

[45] Nov. 24, 1981

[54] METHOD FOR MEASURING THE IONIC ACTIVITIES IN WATER WITH A DIFFERENTIAL PRESSURE TRANSDUCERS

[75] Inventor: Nev A. Gokcen, Albany, Oreg.

[73] Assignee: The United States of America as represented by the Secretary of the Interior, Washington, D.C.

[21] Appl. No.: 147,690

[22] Filed: May 7, 1980

[51] Int. Cl.$^3$ .............................................. G01N 7/14
[52] U.S. Cl. ...................................... 73/64.2; 73/15.4
[58] Field of Search ....................... 73/64.2, 747, 15.4

[56] References Cited

U.S. PATENT DOCUMENTS

| 3,134,262 | 5/1964 | Dworzan et al. | 73/749 |
| 3,313,157 | 4/1967 | Gilson | 73/747 |
| 3,459,043 | 8/1969 | Young | 73/749 |

FOREIGN PATENT DOCUMENTS

| 505916 | 10/1976 | U.S.S.R. | 73/64.2 |
| 605152 | 4/1978 | U.S.S.R. | 73/64.2 |

Primary Examiner—Donald O. Woodiel

Attorney, Agent, or Firm—Thomas Zack; Donald A. Gardiner

[57] ABSTRACT

An apparatus and method that gives very accurate measurements which allow one to determine the values of ionic activities of aqueous electrolyte solutions. To obtain these accurate measurements, moderately accurate measurements of vapor pressure differences between pure water (or a reference liquid) and the aqueous electrolytes is first obtained. A container with a known solution of nonvolatile electrolyte in water, i.e., a solution of known composition, is connected to one side of a differential pressure transducer, the other side of which is connected to a second container with a deionized double distilled water. Next, the gas in the containers and dissolved in liquids is evacuated by using a mechanical pump and the containers are immersed in a temperature controlled medium. At this point in time, the differential pressure transducer measures the difference in pressure. This reading may be used to obtain the vapor pressure of the solution and then determine corresponding ionic activities of the electrolyte in the solution.

3 Claims, 1 Drawing Figure

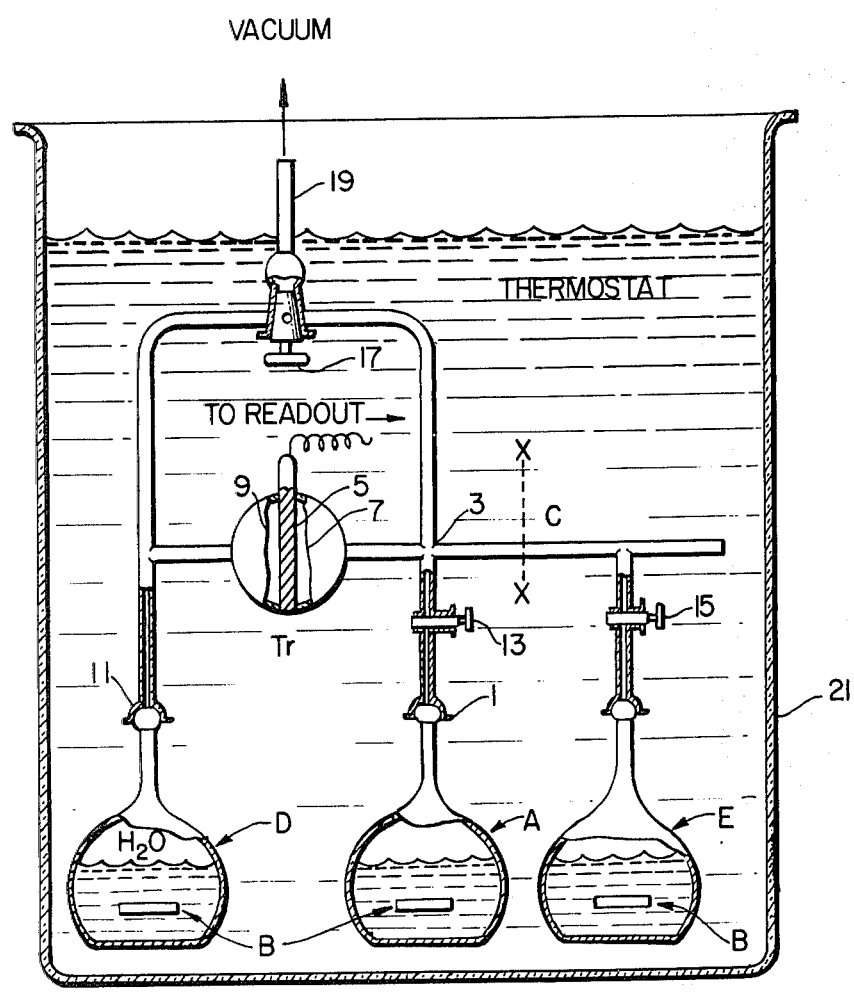

METHOD FOR MEASURING THE IONIC ACTIVITIES IN WATER WITH A DIFFERENTIAL PRESSURE TRANSDUCERS

BACKGROUND OF THE INVENTION

1. Field of the Invention

This invention is a method and accompanying apparatus which allows the determination with great accuracy of the ionic activities of aqueous electrolyte solutions.

2. Description of the Prior Art

The prior art teaches it is old to measure the pressure difference between a solution and a reference liquid to determine the characteristics of the solution. For example, the USSR Pat. No. 505-916—the closest known prior art—discloses two vessels filled with liquid fuels and placed in a thermostat. Taps are employed as valves for each vessel and each vessel is connected to each leg of a single U-shaped mercury pressure gauge or manometer which can read the pressure difference between the vapors of the liquids. In that patent the reference liquid is fuel and has a known vapor pressure. Using this information and the pressure difference reading allows the calculation of the saturation vapor—and hence quality—of the test liquid.

The essential difference between this reference and my invention resides in the fact that the patent can yield results having no better than a 10 percent accuracy and it does not employ aqueous electrolytes as the test liquids or solutions. Contrary to these prior art results, my invention can achieve an accuracy of 0.01 percent in the pressure difference measurement to yield by calculation an accuracy of 0.0008 percent in the ionic activity measurement. It achieves this result by using very accurate measurements of the pressure difference and then uses the known vapor pressure of pure water to very accurately determine the lower vapor pressure for the test solution. Pure water is also used as a standard for calibrating the pressure readings. This determined lower vapor pressure reading can then be used to very accurately arrive at many determinative results. For example, the ionic activity, heat of solution of each electrolyte, construction of the vapor-liquid phase diagram for each binary and multicomponent solution, and the heat of vaporization of water from a given solution.

SUMMARY OF THE INVENTION

My invention is a method which employs the principle of making a moderately accurate measurement of the vapor pressure difference between a known liquid and a liquid solution under test to arrive at a highly accurate value of the vapor pressure for the liquid solution under test. It achieves this result by making the pressure difference measurement with a pressure differential transducer and also obtaining the upper limit vapor pressure from standard tables for the reference liquid which is pure water in the present embodiment. To insure accuracy of the derived pressure result, the entire assembly is immersed in a medium which is very accurately thermostatically controlled. By obtaining readings at two or more temperatures, the readings can be used to calculate the heat of vaporization and many other characteristics of the liquid solution.

The primary object of this invention is a highly accurate and very rapid method used to measure vapor pressure of a liquid solution at different temperatures.

DESCRIPTION OF THE DRAWINGS

The FIGURE schematically illustrates the preferred embodiment apparatus set up used to practice the method of the invention.

In the illustrated embodiment there is a glass bulb container A having a known solution of nonvolatile electrolytes in water and a magnet-bar B used to stir the solution by using an external magnet. The upper opening of container A is in communication with a ball and socket joint 1 or any other type of joint that is lubricated by grease to fit into the remainder of the system. Suitable tubing 3 connects the vapor from the solution in fluid bulb A via kovar-glass cross joints to the differential transducer Tr. In the illustrated embodiment this transducer employed a remote (not shown) digital electronic readout and a diaphram 5 between volumes 7 and 9 to arrive at the pressure difference reading between bulb A containing the solution and bulb D containing pure water, or a reference fluid. With the commercially available pressure transducer (for example Pressure Transducer Model No. 315 BH-10 SP, MKS instruments, Inc. Burlington, Mass.) used in the preferred embodiment, a reading accuracy of better than 0.001 percent is possible. Above the system a vacuum is created to better than one millionth atmosphere. Illustrated in the system is bulb container D, identical to bulb-A, which contains deionized double-distilled water and the magnetic stirrer B (magnet-bar). An appropriate joint 11, various stopcocks (13, 15, and 17), and tubular connections permit the gaseous evacuation of the system to the upper vacuum via outlet 19.

All of the foregoing bulbs, tubes, transducer, stopcocks, stirrers, etc. form the system which is placed in the thermostat controlled medium of container 21. This medium employs water or some organic liquid to encase the system and maintain its components at the same temperature. Appropriate additional means (not shown) are employed to stir this liquid which may be similar to the magnetic stirrers B. In the preferred embodiment the thermostat employed was specifically designed and constructed by me to keep the system's temperature accurate to within +0.01 degrees C. Stirring takes place at approximately 100 revolutions per minute in the solution with the magnet bar and approximately 300 revolutions per minute in the thermostat. The important criterion for stirring is the temperature uniformity of the entire assembly, namely the thermostat, the bulbs and their contents. By controlling the temperature of the system very accurately and obtaining the vapor pressure of the pure water in bulb D from appropriate and known to be very accurate tables, the activity of the water ($a_w$) in bulb A can be determined by the relationship:

$$a_w = (P^o - \Delta P)/p^o \qquad (1)$$

where $P^o$ is the vapor pressure of the pure water in bulb D as read from a published table at a given controlled temperature and $\Delta P$ the pressure difference as read from the transducer's readout.

For example, if the vapor pressure for the water in bulb D was 25 Torr at a specific temperature set by the thermostat 21 and the transducer read a pressure difference $\Delta P$ of 2 Torr with an accuracy of 0.01 percent. Then, the value of the vapor pressure of the gas given off from bulb A would be known with an accuracy of 0.0009 percent.

To the right of the vertical dashed line X—X is shown the tubular connection C and an additional bulb E which can, as a very important option, also be employed. This bulb is identical to bulbs A and D. It also has a magnetic stirrer B. The solution in bulb E has a different molarity from A and D and as such allows the determination of its unknown vapor pressure by employing the same method outlined and utilized for bulbs D and A. In fact it is possible to have many more additional bulbs as permitted by space and by convenience in operation, to obtain several sets of data at various temperatures during one expermental run. Once the vapor pressure for the unknown liquid is determined using $P^o$-$\Delta P$ at two or three temperatures; then the heat of vaporization of water from a given solution can be calculated; the heat of solution of each electrolyte can be arrived at; the ionic activities can be known; and one can construct a vapor-liquid phase diagram for each set of binary and multicomponent solutions. Further details on how these determinations can be made from the data of formula (1) and exactly what each means can be had by reading Chapter XIII pages 337 et seq. of "Thermodynamics" by N. A. Gokcen published by Techscience Incorporated, Hawthorne California, 1975.

It should be clear that the invention allows one to use the data obtained from a moderately accurate measurement of pressure difference between pure water and an aqueous electrolyte to yield very highly accurate values of ionic activities of aqueous electrolyte solutions. Other uses using other known reference solutions instead of water, and other solutions instead of water solutions are also possible. For example, pure carbon disulfide can be used instead of pure water in bulb D and a solution of sulfur in carbon disulfide can be used as a solution in bulb A.

Although this invention has been disclosed with respect to a specific embodiment, none of the disclosed limitations should be used to limit the scope and extent of the invention which is to be measured only by the claims which follow.

I claim:

1. A method of accurately determining the vapor pressure of a solution comprising the steps of:
    (a) placing the solution in a container having a fluid communication system maintained at a known controllable temperature;
    (b) placing a reference liquid with a known vapor pressure in the same system as the solution at the same temperature;
    (c) stirring the solution and reference liquid of steps (a) and (b) by over 100 revolutions per minute;
    (d) measuring the vapor pressure difference in the system between the liquid and the solution using a pressure difference transducer; and
    (e) based upon the results of step (d) and the known vapor pressure of the liquid, determining the vapor pressure of the solution for the given temperature of the system.

2. The method of claim 1 wherein the vapor pressure of step (b) is that of deionized double-distilled water and the solution of step (a) is a solution of known composition containing nonvolatile electrolytes in water.

3. The method of claim 1 including the additional step (f) of completing steps (a) to (e) at two or more distinct different known temperatures.

* * * * *